US008895625B2

(12) United States Patent
Alkharfy et al.

(10) Patent No.: US 8,895,625 B2
(45) Date of Patent: Nov. 25, 2014

(54) PROTECTIVE EFFECT OF THYMOQUINONE IN SEPSIS

(75) Inventors: Khalid M Alkharfy, Riyadh (SA); Nasser M. Al-Daghri, Riyadh (SA); Omar S. Al-Attas, Riyadh (SA); Majed S. Alokail, Riyadh (SA)

(73) Assignee: King Saud University, Riyadh (SA)

( * ) Notice: Subject to any disclaimer, the term of this patent is extended or adjusted under 35 U.S.C. 154(b) by 417 days.

(21) Appl. No.: 12/560,587

(22) Filed: Sep. 16, 2009

(65) Prior Publication Data
US 2010/0273893 A1 Oct. 28, 2010

(30) Foreign Application Priority Data
Apr. 23, 2009 (EP) .................................... 09005726

(51) Int. Cl.
*A61K 31/122* (2006.01)
*A61P 29/00* (2006.01)
*C07C 49/543* (2006.01)

(52) U.S. Cl.
CPC .................................... *A61K 31/122* (2013.01)
USPC ........... 514/690; 514/171; 514/547; 424/764; 568/377

(58) Field of Classification Search
CPC .... A61K 31/122; A61K 36/71; A61K 31/232
USPC ............ 514/690, 171, 547; 424/764; 568/377
See application file for complete search history.

(56) References Cited

U.S. PATENT DOCUMENTS

2003/0060454 A1* 3/2003 Kandil .......................... 514/171

FOREIGN PATENT DOCUMENTS

WO 2006024545 A1 3/2006

OTHER PUBLICATIONS

Chamberlain lecture, Aug. 24, 2004, downloaded from the internet on Aug. 10, 2011, URL: http://www.atsu.edu/faculty/chamberlain/website/lectures/lecture/sepsi.htm.*
Kokoska et al (Journal of Food Protection, vol. 71, No. 12, 2008 pp. 2475-2480.*
El Gazzar, M.A. et al., "Thymoquinone attenuates proinflammatory responses in lipopolysaccharide-activated mast cells by modulating NF-kappaB nuclear transactivation," Biochimica et Biophysica Acta, vol. 1770, Nr. 4, 2007, pp. 556-564, XP005900229.
Alsaif, M.A., "Effect of *Nigella sativa* Oil on Metabolic Responses to Prolonged Systemic Injury in Rats," Journal of Biological Sciences, vol. 8, Nr. 6, 2008, pp. 974-983, XP009118155.
Yildiz, F. et al., "*Nigella sativa* relieves the deleterious effects of ischemia reperfusion injury on liver," World Journal of Gastroenterology, vol. 14, Nr. 33, 2008, pp. 5204-5209, XP002531818.

(Continued)

*Primary Examiner* — Savitha Rao
(74) *Attorney, Agent, or Firm* — Lowe Hauptman & Ham LLP (57) ABSTRACT

The present invention refers to thymoquinone, a main constituent of the volatile oil of *Nigella sativa*, and its protective effect against sepsis syndrome morbidity, mortality and associated organ dysfunctions. In particular, the present invention refers to thymoquinone for use in the prevention and/or treatment of sepsis syndrome. The present invention further refers to a pharmaceutical composition and a kit.

9 Claims, 5 Drawing Sheets

(56) References Cited

OTHER PUBLICATIONS

El Gazzar, M.A., "Thymoquinone suppresses in vitro production of IL-5 and IL-13 by mast cells in response to lipopolysaccharide stimulation," Inflammation Research, Official Journal of the International Association of Inflammation Societies, The European Histamine Research Society, vol. 56, Nr. 8, 2007, pp. 345-351, XP019531449.

Liu, M. et al., "Growth-Inhibiting Activity of Anthraquinones and Benzoquinones Against Methicillin-Resistant *Staphylococcus aureus* (MRSA)," Dokkyo Journal of Medical Sciences, vol. 23, Nr. 2, 1996, pp. 85-93, XP000908978.

Lai, P.K. et al., "Antimicrobial and Chemopreventive Properties of Herbs and Spices," Current Medicinal Chemistry, vol. 11, Nr. 11, 2004, pp. 1451-1460, XP009117713.

Aljabre, S.H.M. et al., "Antidermatophyte activity of ether extract of *Nigella sativa* and its active principle, thymoquinone," Journal of Ethnopharmacology, vol. 101, Nr. 1-3, 2005, pp. 116-119, XP025270010.

Inouye, S. et al., "Evaluation of the effect of terpenoid quinones on *Trichophyton mentagrophytes* by solution and vapor contact," Journal of Infection and Chemotherapy, Official Journal of the Japanese Society of Chemotherapy and the Japanese Association for Infectious Diseases, vol. 12, Nr. 2, 2006, pp. 100-104, XP019374935.

El-Dakhakhny, M. et al., "Protective effect of *Nigella sativa* oil and clindamycin against production of tumor necrosis factor-alpha and liver injury in murine septic peritonitis," Naunyn-Schmiedeberg's Archives of Pharmacology, vol. 362, Nr. 4-5, 2000, p. 12, XP009118158.

\* cited by examiner

PROTECTIVE EFFECT OF THYMOQUINONE IN SEPSIS

RELATED APPLICATIONS

The present application is based on, and claims priority from, European Application Number EP09005726, filed Apr. 23, 2009, the disclosure of which is hereby incorporated by reference herein in its entirety.

The present invention refers to thymoquinone, a main constituent of the volatile oil of *Nigella sativa*, and its protective effect against sepsis syndrome morbidity, mortality and associated organ dysfunctions. In particular, the present invention refers to thymoquinone for use in the prevention and/or treatment of sepsis syndrome. The present invention further refers to a pharmaceutical composition and a kit.

BACKGROUND OF THE INVENTION

Sepsis, defined as the systemic host response to microorganisms in previously sterile tissues, is a syndrome related to severe infections and is characterized by end-organ dysfunction away from the primary site of infection. To meet the definition of sepsis, patients need to satisfy at least two of the Systemic Inflammatory Response Syndrome (SIRS) criteria in association with having a suspected or confirmed infection.

The clinical diagnostic parameters of septic patients as defined at the International Sepsis Definitions Conference in 2001 include the following (Levy et al. 2001):

| [a]Infection (documented or suspected) and some (i.e., two or more) of the following[b]: |
|---|
| General parameters |
| Fever (core temperature >38.3° C.)<br>Hypothermia (core temperature <36° C.<br>Heart rate >90 bpm or >2 SD above the normal value for age<br>Tachypnea: >30 bpm<br>Altered mental status<br>Significant edema or positive fluid balance (>20 ml/kg over 24 h)<br>Hyperglycemia (plasma glucose >110 mg/dl or 7.7 mM/l) in the absence of diabetes |
| Inflammatory parameters |
| Leukocytosis (white blood cell count >12,000/µl)<br>Leukopenia (white blood cell count <4,000/µl)<br>Normal white blood cell count with >10% immature forms<br>Plasma C reactive protein >2 SD above the normal value<br>Plasma procalcitonin >2 SD above the normal value |
| Hemodynamic parameters |
| Arterial hypotension[b] (systolic blood pressure <90 mmHg, mean arterial pressure <70 mmHg, or a systolic blood pressure decrease >40 mmHg in adults or <2 SD below normal for age)<br>Mixed venous oxygen saturation >70%[b]<br>Cardiac index >3.5 1 min$^{-1}$ m$^{-2c,d}$ |
| Organ dysfunction parameters |
| Arterial hypoxemia (PaO2/FIO2 <300)<br>Acute oliguria (urine output <0.5 ml kg$^{-1}$ h$^{-1}$ or 45 mM/l for at least 2 h)<br>Creatinine increase ≥ 0.5 mg/dl<br>Coagulation abnormalities (international normalized ratio >1.5 or activated partial thromboplastin time >60 s)<br>Ileus (absent bowel sounds)<br>Thrombocytopenia (platelet count <100,000/µl) |
| [a]Infection (documented or suspected) and some (i.e., two or more) of the following[b]: |
| Hyperbilirubinemia (plasma total bilirubin >4 mg/dl or 70 mmol/l)<br>Tissue perfusion parameters |
| Hyperlactatemia (>3 mmol/l)<br>Decreased capillary refill or mottling |

Figure 1:
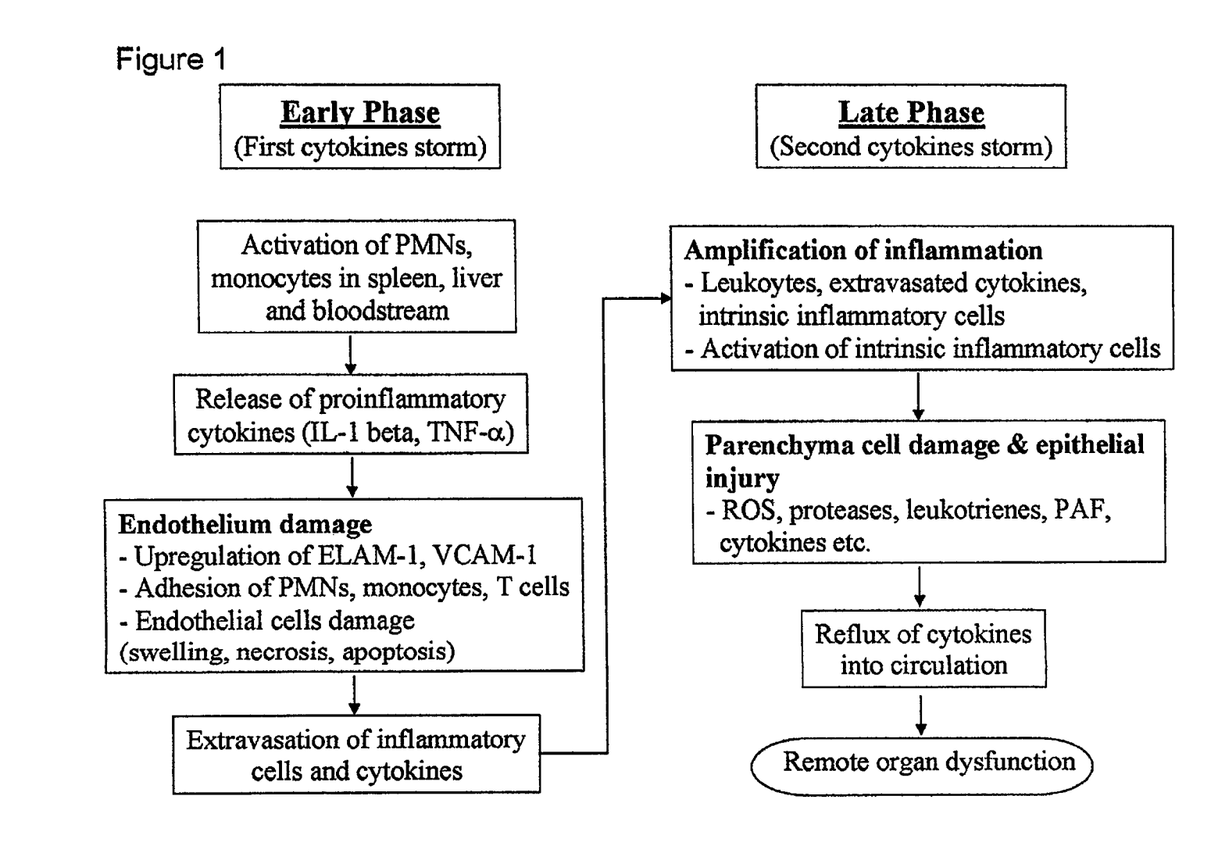
FIG. 1 schematically shows the main pathologic mechanisms in the early and later phases of MODS. ELAM-1 indicates endothelial-leukocyte adhesion molecule 1; PAF, platelet-activating factor; TNF-α, tumor necrosis factor-α; VCAM-1, vascular cell adhesion molecule 1 (Wang and Ma, 2008).

[a]Defined as a pathological process induced by a microorganism
[b]Values above 70% are normal in children (normally 75-80%) and should therefore not be used as a sign of sepsis in newborns or children
[c]Values of 3.5-5.5 are normal in children and should therefore not be used as a sign of sepsis in newborns or children
[d]Diagnostic criteria for sepsis in the pediatric population is signs and symptoms of inflammation plus infection with hyper- or hypothermia (rectal temperature >38.5° C. or <35° C.), tachycardia (may be absent in hypothermic patients) and at least one of the following indications of altered organ function: altered mental status, hypoxemia, elevated serum lactate level, and bounding pulses The normal host response to infection is complex, aiming to both identify and control pathogen invasion and start immediate tissue repair. Both the cellular and humoral immune systems are activated, giving rise to anti-inflammatory and proinflammatory responses. Exacerbating these mechanisms can cause a chain of events that leads to massive liberation of mediators with diffuse endothelial injury, tissue hypo-perfusion, disseminated intravascular coagulation, and refractory shock and eventually progression of a multiple organ dysfunction syndrome (MODS) and possibly death. FIG. 1 shows the main pathologic mechanisms in the early and later phases of MODS.

While almost any microorganism can be associated with sepsis and septic shock, Gram-negative bacteria are common etiologic pathogens. Lipopolysaccharides (LPS) are normal components of the cell wall of Gram-negative bacteria and have been recognized for many years as key risk factors in the development of septic shock syndrome. Many of the adverse effects of LPS in mammals are dependent on the activation of cellular and soluble inflammatory mediators including polymorphonuclear leukocytes (PMNs), and cytokines such as tumor necrosis factor-α (TNF-α) and interleukin-1 (IL-1). It has been shown that PMNs accumulate in tissues after LPS administration, and although they play an important role as a host defense mechanism, they are responsible for mediating LPS-induced tissue injuries. Several lines of evidence now suggested that stimulatory inflammatory cells release a plethora of mediators including reactive oxygen species, proteolytic enzymes and products of lipid peroxidation products.

Morbidity and mortality remain unacceptably high despite increasing knowledge about the pathophysiological pathways and processes involved in sepsis and improved hospital care. It still is one of the most prevalent causes of intensive care units (ICU) morbidity and mortality worldwide. More than 750,000 sepsis cases occur in the United States every year, leading to approximately 220,000 deaths; similar incidences have also been reported in Europe and around the world. In fact, the mortality rates of septic shock could be as high as 50% or up to 75% on longer follow-ups.

Clinical management usually begins with prompt recognition, determination of the probable infection site, early administration of antibiotics, low-dose corticosteroids, and resuscitation protocols. Corticosteroids, the most potent anti-inflammatory class of drugs, have demonstrated a modest decrease in mortality (absolute reduction of 10%) with lower doses in septic shock. Other anti-inflammatory drugs such as non-steroidal anti-inflammatory drugs (NSAIDs) did not show to be helpful in ameliorating sepsis syndrome.

Furthermore, in attempts to find efficacious drugs that reduce mortality, a large number of immunomodulatory agents have been studied in experimental and clinical settings. However, the vast majority of these trials showed little success in reducing the overwhelmingly high mortality rates of septic shock patients. Only one immunomodulatory drug, drotrecogin alfa (a recombinant form of human activated protein C, Xigris®) has been approved as an adjunct to standard care in sepsis patients with evidence of organ dysfunction. The improved survival rate is also clinically modest, and only some patients with severe disease will benefit. The PROWESS trial, which suffered from few flaws, indicated a 6% absolute decrease in mortality rate (19% relative risk reduction) compared to placebo; this difference is somewhat remarkable considering that no other adjunctive treatment modality directed at underlying pathology (including TNF-α monoclonal antibodies, IL-1 antagonists, and p55 TNF receptor IgG1 fusion protein) has been shown to significantly alter clinical outcome in severe sepsis. Later studies reported that drotrecogin alfa is not effective in patients with a low risk of death or in pediatric patients. Administration of drotrecogin alfa is associated with an increased risk. In addition, a post hoc analysis of a subgroup of patients who had undergone recent surgery (i.e., within 30 days before enrolment) and had single-organ dysfunction indicated that the patients in this subgroup who received drotrecogin alfa had higher 28-day mortality rates than did the patients in this group who received placebo (20.7% vs. 14.1%, P=0.03). In response to these results and further analysis of the PROWESS data which suggested a lesser efficacy in surgical patients, an additional warning was introduced to the prescribing information for drotrecogin alfa, stating that the drug should not be used in patients with recent surgery and single organ dysfunction.

These findings and experiences indicate that the pathogenesis of sepsis syndrome is highly complex, and it involves multiple immune responses including the activation of cytokines and the generation of reactive free radicals. Therefore, it is important to continue the development of newer agents to potentially identify a clinically relevant anti-sepsis drug.

Thus, the object of the present invention is to provide new means and methods which are useful in the prevention and/or treatment of sepsis syndrome.

SUMMARY OF THE INVENTION

The object of the present invention is solved by a thymoquinone compound or a tautomer or an analogue or a derivative or a pharmaceutically acceptable salt thereof for use in the prevention and/or treatment of sepsis syndrome or a condition associated with sepsis syndrome in a subject.

The object of the present invention is further solved by a use of a thymoquinone compound or a tautomer or an analogue or a derivative or a pharmaceutically acceptable salt thereof in the preparation of a medicament for the prevention and/or treatment of sepsis syndrome or a condition associated with sepsis syndrome in a subject.

The object of the present invention is further solved by a pharmaceutical composition comprising a thymoquinone compound or a tautomer or an analogue or a derivative or a pharmaceutically acceptable salt thereof for use in the prevention and/or treatment of sepsis syndrome or a condition associated with sepsis syndrome in a subject.

The object of the present invention is further solved by a pharmaceutical composition comprising a thymoquinone compound or a tautomer or an analogue or a derivative or a pharmaceutically acceptable salt thereof for use in the preparation of a medicament for the prevention and/or treatment of sepsis syndrome or a condition associated with sepsis syndrome in a subject.

The object of the present invention is further solved by a method of prevention and/or treatment of sepsis syndrome or a condition associated with sepsis syndrome by administering a thymoquinone compound or a tautomer or an analogue or a derivative or a pharmaceutically acceptable salt thereof to a subject.

The object of the present invention is further solved by a method of prevention and/or treatment of sepsis or a condition associated with sepsis by administering a pharmaceutical composition comprising a thymoquinone compound or a tautomer or an analogue or a derivative or a pharmaceutically acceptable salt thereof to a subject.

The object of the present invention is further solved by a kit comprising a thymoquinone compound or a tautomer or an analogue or a derivative or a pharmaceutically acceptable salt thereof or comprising a pharmaceutical composition comprising a thymoquinone compound or a tautomer or an analogue or a derivative or a pharmaceutically acceptable salt thereof for use in the prevention and/or treatment of sepsis syndrome or a condition associated with sepsis syndrome in a subject, the kit further comprising a package and/or a package insert indicating said use.

In one embodiment, the condition of sepsis syndrome is severe sepsis or septic shock.

In one embodiment, the condition associated with sepsis syndrome is selected from the group consisting of an organ dysfunction, preferably a kidney dysfunction or a liver dysfunction, a multiple organ dysfunction syndrome (MODS), an acute respiratory distress syndrome (ARDS), and disseminated intravascular coagulation (DIC).

In one embodiment, the sepsis syndrome is induced by a bacterium or more than one bacterium selected from the group consisting of Gram-negative bacteria and Gram-positive bacteria.

In one embodiment, the Gram-negative bacterium is selected from the group consisting of *Escherichia coli*, *Klebsiella* species, *Serratia* species, *Enterobacter* species, *Proteus* species, *Pseudomonas aeruginosa*, *Haemophilus influenzae*, *Neisseria* species, and *Listeria* species.

In one embodiment, the Gram-positive bacterium is selected from the group consisting of *Staphylococcus aureus*, *Streptococcus pneumoniae*, coagulase-negative Staphylococci, *Enterococcus* species, *Streptococcus pyogenes*, and *Streptococcus viridans*.

In one embodiment, the bacterium is a Gram-negative bacterium, preferably *E. coli*.

In one embodiment, the sepsis syndrome is induced by LPS.

In one embodiment, the sepsis syndrome is induced by a microorganism or more than one microorganism selected from the group consisting of anaerobic bacteria, fungi, rickettsiae, chlamydiae, mycoplasma, spirochetes, and viruses.

In one embodiment, the subject is a mammal, preferably a human.

In one embodiment, the thymoquinone compound or the pharmaceutical composition is for administration of the thymoquinone compound to a mammal, preferably a mouse, at a dosage in the range of about 0.5 to 2 mg/kg body weight, preferably at a dosage of about 2 mg/kg body weight.

In one embodiment, the thymoquinone compound or the pharmaceutical composition is for administration of the thymoquinone compound to a human at a dosage in the range of about 0.05 to 0.25 mg/kg body weight, preferably at a dosage of about 0.25 mg/kg body weight.

In one embodiment, the thymoquinone compound is administered to a mammal, preferably a mouse, at a dosage in the range of about 0.5 to 2 mg/kg body weight, preferably at a dosage of about 2 mg/kg body weight.

In one embodiment, the thymoquinone compound is administered to a human at a dosage in the range of about 0.05 to 0.25 mg/kg body weight, preferably at a dosage of about 0.25 mg/kg body weight.

In one embodiment, the thymoquinone compound is administered in one single dose, or is administered consecutively in more than one single doses, or is administered continuously, i.e. by infusion.

In one embodiment, the pharmaceutical composition is for oral or parenteral administration. Parenteral administration preferably is by intravenous, intramuscular or subcutaneous administration. Intravenous administration can be either by infusion or bolus injection. Other routes of administration are also considered, such as sublingual, rectal, vaginal or topical administration or administration by inhalation.

In one embodiment, the thymoquinone compound or the pharmaceutical composition is comprised by an infusion solution or an injection solution. In an alternative embodiment, the thymoquinone compound or the pharmaceutical composition is comprised by a pharmaceutical dosage form selected from the group consisting of a tablet, a capsule, a caplet, a suppository, an ointment, and a patch. In one embodiment, the thymoquinone compound or the pharmaceutical composition is comprised in a controlled-release dosage form, preferably a sustained-release dosage form.

In one embodiment, the pharmaceutical composition or the kit further comprises a drug or more than one drug selected from the group consisting of an antibiotic, a corticosteroid and/or an immunomodulatory drug.

The term "sepsis" describes a condition defined as "a Systemic Inflammatory Response Syndrome (SIRS) secondary to infection". Such a condition is characterized by a manifested infection induced by microorganisms, preferably bacteria or fungi, by parasites or by viruses or prions. The term comprises different forms of sepsis, e.g. urosepsis, sepsis due to pneumonia, intraabdominal infection, postoperative sepsis, sepsis due to invasion of a foreign body, sepsis due to bone marrow insufficiency or neutropenia, cholangiosepsis, sepsis after skin injury, burn or dermatitis, dentogenic or tonsillogenic sepsis. As used herein, the terms "sepsis" and "septic syndrome" are equivalent and interchangeable.

The more general term SIRS describes a generalized hyper-inflammatory reaction of diverse geneses, e.g. infection, burn and trauma. Thus, "sepsis" is a particular form of SIRS, namely a SIRS characterized by infection of normally or physiologically sterile tissue.

Particular forms of the condition of sepsis are "severe sepsis" and "septic shock". "Severe sepsis" is defined as "a sepsis associated with (multiple) organ dysfunction, hypoperfusion, or hypotension". "Septic shock" is defined as "a sepsis with hypotension, despite fluid resuscitation, along with the presence of perfusion abnormalities".

The term "tautomer" refers to thymohydroquinone, i.e. a tautomer of thymoquinone.

The term "analogue" refers to a compound which is similar to another compound in structure and/or function.

The term "derivative" refers to a compound differing from another compound by a structural modification, for example by replacement of one atom or a group of atoms or a functional group with another group of atoms or functional group.

The goals of the work relating to the present invention were to evaluate, for the first time, the effect of thymoquinone on sepsis-related mortality using an animal model, and to assess its effect on important organ failure biomarkers during sepsis syndrome in vivo.

Figure 2:
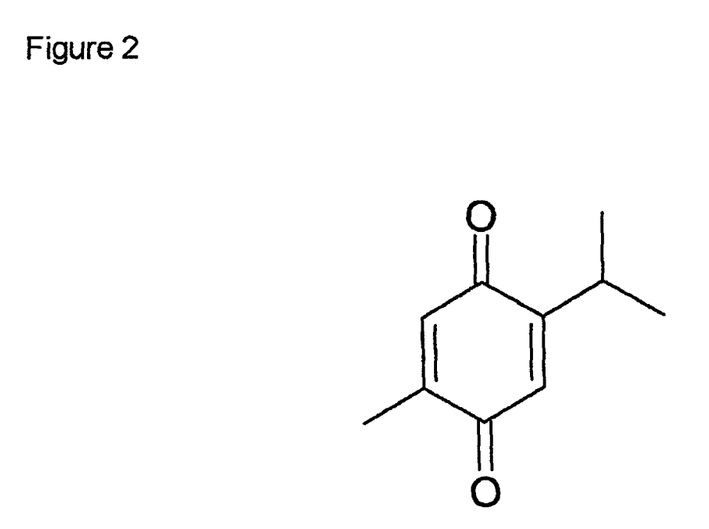
FIG. 2 shows the chemical structure of thymoquinone.

Thymoquinone (2-isopropyl-5-methyl-1,4-benzoquinone) as depicted in FIG. 2 is the main constituent of the volatile oil of *Nigella sativa*. It has been studied for its cardiovascular, respiratory and anti-inflammatory effects. Thymoquinone was also shown to be cytotoxic to both parental and multidrug resistant tumor cells in vitro.

Since sustained production of reactive oxygen species including nitric oxide and superoxide anion during sepsis can cause oxidative cellular damage, the positive effects of thymoquinone in sepsis syndrome described by the present invention can be can be attributed, at least partially, to its ability to function as antioxidant in biology redox cycling between quinine and hydroquinone, and this properties may shield different biological components against the harmful effects of different reactive radical species. Therefore, thymoquinone could be a panacea for sepsis and a strong candidate for further development as a novel drug to protect against and/or treat this devastating condition for which no drug has specifically been proven to be highly effective until to date.

DETAILED DESCRIPTION OF THE INVENTION

EXAMPLES

Example 1

Mouse Model of Sepsis 1.1 Endotoxin Sepsis Model (LPS *Escherichia coli* O111:B4)

Two groups of animals (ten mice each) weighing ~25 g were treated intraperitoneally with 1 or 2 mg/kg (single dose) of thymoquinone prepared in 10% DMSO; a control group (treated with only 10% DMSO) was also simultaneously run. Four hours after thymoquinone treatment, all groups were challenged with 2 mg/kg endotoxin (lipopolysaccharide, LPS) prepared in normal saline. Mortality of groups was followed for 4 days, and survival (primary endpoint) was calculated using Kaplan-Meier analysis.

Figure 3:
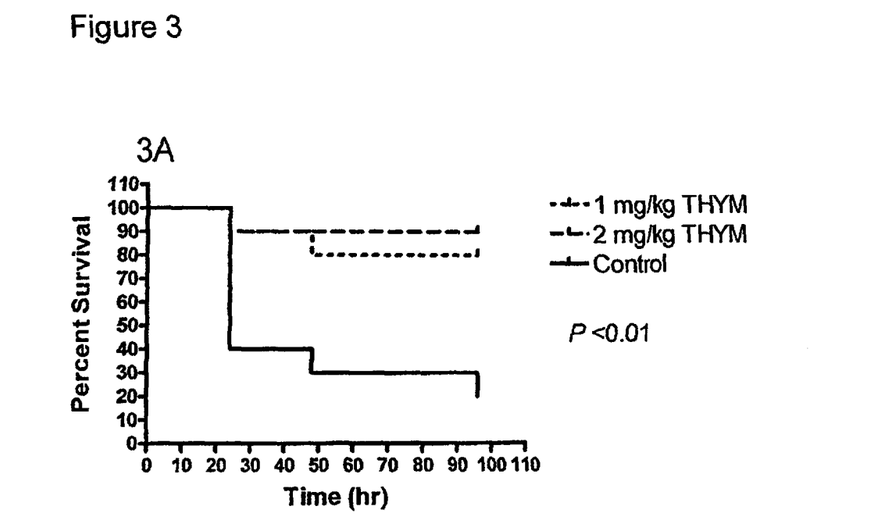
FIG. 3 shows Kaplan-Meier survival analyses following LPS challenge (FIG. 3A) or *E. coli* challenge (FIG. 3B).

As shown in FIG. 3A, thymochinone provided a protective effect against mortality in endotoxin induced sepsis with about 80% (1 mg/kg) and 90% (2 mg/kg) protection efficacy, respectively ($P<0.01$).

1.2 Gram-Negative Bacteria Sepsis Model

Two groups of animals (twelve mice each) weighing ~25 g were treated intraperitoneally with 0.75 or 1 mg/kg/day (for three days) of thymoquinone prepared in 10% DMSO; a control group (treated with only 10% DMSO) was also simultaneously run. Four hours after thymoquinone treatment, all groups were challenged with 2 µl/g *E. coli* (ATCC-25992, $1.5 \times 10$ CFU/ml) prepared in normal saline. Mortality in treated groups was followed for 2 days, and survival (primary endpoint) was calculated using Kaplan-Meier analysis.

As shown in FIG. 3B, thymochinone provided a protective effect against mortality in sepsis induced by Gram-negative bacteria with about 90% (0.75 or 1 mg/kg) protection efficacy ($P<0.01$).

These data demonstrate that thymoquinone has a very potent protective effect against sepsis mortality that reaches up to 80-90%. This activity is apparently not related to any antimicrobial activity of thymoquinone as evident by a similar protective effect seen following LPS administration.

Example 2

Immunological and Biochemical Analysis

In another set of experiments and after 6 h of *E. coli* administration, animals were lightly anesthetized with ether, and blood samples were collected, centrifuged and the resultant plasma were stored at $-80°$ C. and used within 48 h. The levels of TNF-α, IL-1α, IL-2 and IL-10 were determined using an ELISA technique. Important biochemical parameters including blood serum creatinine, blood urea nitrogen, alanine transferase (ALT), albumin, and total lactate dehydrogenase (LDH) and creatinine kinase (CK) were also assessed in treated animals using commercially available kits according to the manufacturer's directions.

The data show that induced sepsis also causes injuries and disruption in the biochemical functions of many organs such as kidney and liver that was manifested as an elevation in serum levels of serum creatinine and blood urea nitrogen, ALT, and total LDH and CK.

Figure 4:
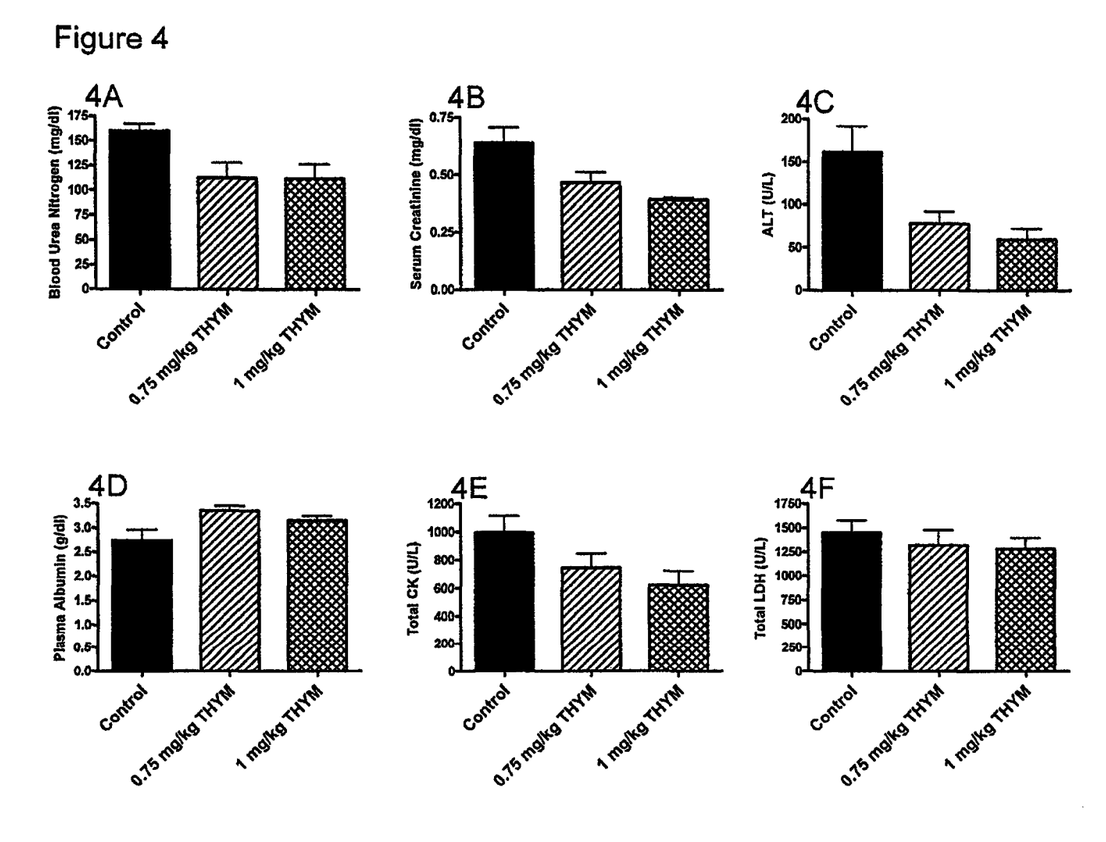
FIG. 4 shows the results of biochemical blood analyses following *E. coli* administration. Blood urea nitrogen (marker of kidney dysfunction) (FIG. 4A); serum creatinine (marker of kidney dysfunction) (FIG. 4B); alanine transferase (marker of liver dysfunction) (FIG. 4C); plasma albumin (marker of oncotic pressure) (FIG. 4D); total creatinine kinase (marker of tissue injury) (FIG. 4E); total lactate dehydrogenase (marker of tissue injury) (FIG. 4F).

FIG. 4 shows the organ protective effects of thymoquinone in sepsis caused by *E. coli* bacteria. Important reductions are seen in kidney dysfunction biomarkers (measured by blood urea nitrogen and serum creatinine levels), liver dysfunction biomarkers (measured by plasma albumin and alaninine transferase) with improvement in albumin level, and in total creatinine kinase and lactate dehydrogenease (markers for tissue injury).

Figure 5:
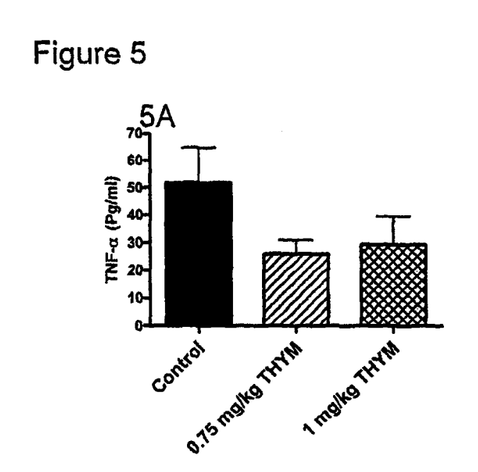
FIG. 5 shows the results of immunological serum analyses following *E. coli* administration. TNF-α (FIG. 5A); IL-1 α (FIG. 5B); IL-2 (FIG. 5C); IL-10 (FIG. 5D).

FIG. 5 shows the immunomodulatory effects of thymoquinone in sepsis induced by *E. coli* bacteria. Significant reductions are seen in the levels of mediators and biomarkers of inflammation including TNF-α, IL-1α, IL-2 and IL-10.

Example 3

Estimation of Effective Dosages in Humans

Allometric scaling relates dosing information to total body weight across species using a power equation. Given an allometric relationship in animals, one can use this relationship to predict a starting dose in man that may yield desirable exposures: $Dose_{man} = Dose_{animal} * (Wt_{man}/Wt_{animal})^{0.75}$.

On the basis of the results obtained from the mouse model, effective dosages of thymoquinone in humans were estimated using allometric scaling. According to the body weight ratio of man to mouse, a similar effect is to be expected in humans at dosages between 0.05 and 0.25 mg/kg. Due to allometry, the effective dosages estimated for humans are smaller than that obtained for mice.

REFERENCES

1. Cepinskas G, Wilson J X. Inflammatory response in microvascular endothelium in sepsis: role of oxidants. J Clin Biochem Nutr 2008; 42(3):175-84.
2. Karimi G, Fatehi Z, Gholamnejad Z. The role of nitric oxide and protein kinase C in lipopolysaccharidemediated vascular hyporeactivity. J Pharm Pharm Sci 2006; 9(1): 119-23.
3. Levy M M, Fink M P, Marshall J C, Abraham E, Angus D, Cook D, Cohen J, Opal S M, Vincent J-L, Ramsay G. 2001 SCCM/ESICM/ACCP/ATS/SIS International Sepsis Definitions Conference Intensive Care Med (2003); 29:530-538.
4. Mansour M A, Nagi M N, El-Khatib A S, Al-Bekairi A M. Effects of thymoquinone on antioxidant enzyme activities, lipid peroxidation and DT-diaphorase in different tissues of mice: a possible mechanism of action. Cell Biochem Funct 2002; 20(2):143-51.
5. Opal S M. The host response to endotoxin, antilipopolysaccharide strategies, and the management of severe sepsis. Int J Med Microbiol 2007; 297(5):365-77.
6. Salem M L. Immunomodulatory and therapeutic properties of the *Nigella sativa* L. seed. Int Immunopharmacol 2005; 5(13-14):1749-70.
7. Seam N, Suffredini A F. Mechanisms of sepsis and insights from clinical trials. Drug Discov Today Dis Mech 2007; 4(2):83-93.
8. Swamy S M, Tan B K. Cytotoxic and immunopotentiating effects of ethanolic extract of *Nigella sativa* L. seeds. J Ethnopharmacol 2000; 70(1):1-7.
9. Vincent J L. Clinical sepsis and septic shock-definition, diagnosis and management principles. Langenbecks Arch Surg 2008.
10. Wang H, Ma S. The cytokine storm and factors determining the sequence and severity of organ dysfunction in multiple organ dysfunction syndrome. Am J Emerg Med 2008; 26(6):711-5.
11. Wittebole X, Collienne C, Castanares-Zapatero D, Laterre P F. Adjunctive therapies for severe sepsis. Int J Antimicrob Agents 2008.

The invention claimed is:

1. A method for treating sepsis in a human being in need thereof comprising:
   systemically administering to the human being an effective amount of thymoquinone for
   a period of time sufficient to provide a protective effect against mortality in sepsis.

2. A method for preventive treatment of a human being against sepsis prior to or upon admission to an intensive care unit of a hospital, said method comprising:
   systemically administering to the human being an effective amount of thymoquinone for a period of time sufficient to provide a protective effect against the occurrence of sepsis.

3. The method for treating sepsis of claim 2, wherein the between 0.05 and 0.25 mg/kg of thymoquinone is administered per day for a period of time sufficient to provide a protective effect against the occurrence of sepsis.

4. The method for treating sepsis of claim 1, wherein the between 0.05 and 0.25 mg/kg of thymoquinone is administered per day for a period of time sufficient to provide a protective effect against mortality in sepsis.

5. The method for treating sepsis of claim 1, wherein the sepsis is induced by lipopolysaccharides.

6. The method for treating sepsis of claim 1, wherein the sepsis is induced by gram-negative bacteria.

7. The method for treating sepsis of claim 1, wherein the sepsis is severe sepsis.

8. The method for treating sepsis of claim 1, wherein the sepsis is septic shock.

9. The method for treating sepsis of claim 1, further comprising systemically administering at least one ingredient selected from an antibiotic, a corticosteroid, and an immunomodulatory drug.

* * * * *